United States Patent
Eryilmaz et al.

(10) Patent No.: US 12,398,509 B2
(45) Date of Patent: Aug. 26, 2025

(54) PROCESS FOR DYEING TEXTILES AND ENZYMES USED THEREIN

(71) Applicant: Sanko Tekstil Isletmeleri San. Ve Tic. A.S., Inegol-Bursa (TR)

(72) Inventors: Jitka Eryilmaz, Inegol-Bursa (TR); Fatih Konukoglu, Inegol-Bursa (TR); Halil Ibrahim Akbas, Inegol-Bursa (TR); Esref Tuncer, Inegol-Bursa (TR); Mahmut Ozdemir, Inegol-Bursa (TR)

(73) Assignee: Sanko Tekstil Isletmeleri San. Ve Tic. A.S., Inegol-Bursa (TR)

(*) Notice: Subject to any disclaimer, the term of this patent is extended or adjusted under 35 U.S.C. 154(b) by 0 days.

(21) Appl. No.: 18/423,707

(22) Filed: Jan. 26, 2024

(65) Prior Publication Data
US 2024/0240390 A1     Jul. 18, 2024

Related U.S. Application Data

(62) Division of application No. 17/148,706, filed on Jan. 14, 2021, now Pat. No. 11,920,290.

(30) Foreign Application Priority Data

Jan. 14, 2020  (EP) .................... 20151830

(51) Int. Cl.
| | | |
|---|---|---|
| *C12N 15/02* | (2006.01) | |
| *C11D 3/386* | (2006.01) | |
| *D06M 16/00* | (2006.01) | |
| *D06P 1/22* | (2006.01) | |
| *D06M 101/06* | (2006.01) | |
| *D06P 5/15* | (2006.01) | |

(52) U.S. Cl.
CPC ....... *D06M 16/003* (2013.01); *C11D 3/38636* (2013.01); *D06P 1/228* (2013.01); *D06M 2101/06* (2013.01); *D06P 5/158* (2013.01)

(58) Field of Classification Search
CPC .... C12N 15/02; C12N 15/09; C12N 15/1055; C12N 9/42; C12N 1/20
See application file for complete search history.

(56) References Cited

U.S. PATENT DOCUMENTS

| | | | |
|---|---|---|---|
| 3,047,352 A | | 7/1962 | Santoro et al. |
| 6,410,498 B1 | * | 6/2002 | Smets ............ C12Y 302/01004 435/193 |

FOREIGN PATENT DOCUMENTS

| | | |
|---|---|---|
| CN | 105126148 A | 12/2015 |
| JP | 2004332148 A | 11/2004 |
| KR | 100660110 | 12/2006 |
| KR | 102027427 | 10/2019 |
| WO | 9740127 A1 | 10/1997 |
| WO | 9740229 A1 | 10/1997 |
| WO | 2008117069 A2 | 10/2008 |
| WO | 2018002379 A2 | 1/2018 |

OTHER PUBLICATIONS

Courtade G et al., "Chemical shift assignments for the apo-form of the catalytic domain, the linker region, and the carbohydrate-binding domain of the cellulose-active lytic polysaccharide monooxygenase ScLPMO10C11", Biomolecular NMR Assignments, vol. 11, No. 2, Aug. 18, 2017.
European Search Report and Written Opinion issued by EPO on Jun. 14, 2021 in corresponding EP application No. 2115188.7.
International Search Report and Written Opinion issued by the EPO on Apr. 22, 2021 in corresponding International application No. PCT/EP2021/050680.
Rioz-Martinez A et al., "Exploring the biocatalytic scope of a bacterial flavin-containing monooxygenase 11", Organic & Biomolecular Chemistry, vol. 9, No. 1, Jan. 1, 2011, p. 1337.

* cited by examiner

*Primary Examiner* — Tekchand Saidha
(74) *Attorney, Agent, or Firm* — Silvia Salvadori, P.C.; Silvia Salvadori

(57) ABSTRACT

The present invention relates to a process wherein one or more dye precursors, e.g., indole, are provided to a textile and converted by one or more enzymes, e.g., an oxidizing enzyme, to provide the textile with a dye, e.g. indigo. At least the oxidizing enzyme is a hybrid enzyme including a binding domain that is suitable to bind the enzyme to the textile and/or increase the affinity of the enzyme for the textile, in particular, a cellulose binding domain (CBD).

5 Claims, No Drawings

PROCESS FOR DYEING TEXTILES AND ENZYMES USED THEREIN

This Non-Provisional Application is a divisional application of U.S. Ser. No. 17/148,706 filed Jan. 14, 2021, which claims priority to and the benefit of European Application No. EP20151830.5 filed on 14 Jan. 2020 the content of which is incorporated herein by reference in its entirety.

FIELD OF THE INVENTION

The present invention relates to a process for dyeing textiles, in particular for dyeing textiles using enzymes.

BACKGROUND OF THE INVENTION

Vat dyes are insoluble dyes that require a reducing agent to be solubilized in water. Conventionally, dyeing with vat dyes includes applying the dye in its soluble, reduced form to the textiles and subsequently oxidizing the dye back to the insoluble form, which confers color to the textile.

Indigo is a vat dye of Formula I:

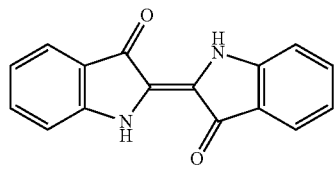

Formula I

Substitutions on the indigo aromatic ring(s) with groups such as halogen, alkyl, alkoxy, amino, aryl, aryloxy, and carbonyl, provide compounds that span in a wide range of colors other than blue, and are part of the so-called indigo derivatives.

A large percentage of indigo and indigo derivatives is produced via synthesis. Heumann synthesis and Pfleger synthesis were the first synthetic routes used for indigo manufacturing at industrial scale; variations of these methods are still in use today. The same synthetic routes are also used to manufacture indigo derivatives.

Synthesis of indigo and derivatives thereof, as well as other vat dyes, can also be carried out by means of enzymes, or by bacteria expressing enzymes.

While precursors of indigo are soluble in aqueous solutions, indigo is not, and it precipitates after its synthesis in aqueous solutions. Therefore, as said above, indigo, as well as its derivatives, is usually reduced to its leuco form, i.e., leuco indigo, which is the reduced, water soluble, form of indigo, to be applied to textiles.

Therefore, industrial dyeing methods using indigo or derivatives thereof as a dye, or using vat dyes in general, comprise treating an aqueous solution comprising suspended indigo or derivatives thereof with reducing agents to obtain an aqueous solution comprising leuco-indigo (or the leuco form of such derivatives thereof). The aqueous solution comprising leuco-indigo is then applied onto textiles. Indigo or indigo derivatives are obtained by oxidation of leuco-indigo or of the leuco form of indigo derivatives on the textile, thus dyeing the textile. Such oxidation can be carried out, for example, with the oxygen in the air, e.g., by exposing the textile provided with, for example, leuco-indigo, to air. Usually, the indigo dyeing process requires several impregnation and oxidation steps to reach the desired shade of color.

The reduction of, for example, indigo to leuco indigo is particularly useful when the textile to be dyed includes a cellulosic material, such as cellulosic fibers or yarns. In fact, reduction of indigo to its water soluble leuco form allows the textile to be provided (e.g., impregnated) with the solution including leuco indigo; subsequently, oxidation of leuco indigo to indigo occurs on the textile.

The reducing agents used to reduce insoluble vat dyes, such as indigo or derivatives thereof, to leuco indigo or the leuco form of indigo derivatives, are harsh chemicals, i.e. hazardous chemicals for users and/or environment, such as sodium hydroxide and sodium hydrosulfite. Additionally, large quantities of reducing salts and hydroxides are used in conventional dyeing processes where indigo or derivatives thereof are used as dyes, thus generating great amounts of wastewater that must be treated before being disposed. This step adds to costs of the dyeing process.

A further problem with known indigo dyeing process is that the textile, especially cellulose, may be damaged by extended exposure to the alkaline process solution and chemical products therein present.

There is thus a need for an improved method for dyeing textiles with vat dyes, in particular with indigo and derivatives thereof, that allows for a reduction in the use of water and of harsh chemicals, for example the reducing agents, without losing dyeing effectiveness, so that the overall cost for vat dyeing and of the waste water treatment processes, if required, is reduced.

SUMMARY OF THE INVENTION

Aim of the present invention is to solve the above-mentioned problems and to provide a process for dyeing textiles that allows for a reduction in the use of harsh chemicals, such as reducing agents, while providing an effective dyeing.

Also aim of the present invention is to provide a process for dyeing textiles that is safe, cost-effective and environmentally friendly.

Another aim of the present invention is to provide a process for dyeing textiles that is more sustainable with respect to conventional dyeing methods.

These and other aims are reached through the present invention that provides a process according to claim 1, namely a process for dyeing a textile, wherein a modified enzyme is involved in the synthesis of indigo and/or indigo derivatives.

The present invention also relates to processes for dyeing textiles, to a dyed textile and to a modified enzyme. The present invention further relates to a textile comprising one or more modified enzymes.

DETAILED DESCRIPTION

The present invention relates to a process for dyeing textiles, in particular textiles including a cellulosic material, comprising the following steps:
a) providing indole or an indole derivative to at least part of said textile;
b) providing at least an oxidizing enzyme to at least part of said textile, whereby said at least part of textile includes said indole or indole derivative and said oxidizing enzyme;
c) converting at least part of said indole or indole derivative to indigo or indigo derivative, thereby dyeing at least part of said textile;

wherein said oxidizing enzyme is an (oxidizing) hybrid enzyme comprising a cellulose-binding domain (CBD).

According to embodiments, indole is applied to the textile as an indole precursor. Namely, step a) comprises a step of providing tryptophan or a tryptophan derivative, and at least a tryptophanase, to said textile, and converting said tryptophan or a tryptophan derivative in the presence of at least a tryptophanase, to obtain said indole or said indole derivative.

Through the process of the invention, it is possible to dye textiles avoiding, or substantially avoiding, the use of harsh chemicals, while obtaining an effective dyeing of the textile.

Moreover, through the process of the invention it is possible to provide insoluble dyes, such as indigo, on a textile in a controlled manner.

In particular, when an oxidizing enzyme comprising a cellulose-binding domain, i.e., an oxidizing hybrid enzyme, is used, an effective dyeing of the textile can be obtained. Without being bound to a specific scientific explanation, an oxidizing enzyme that has been genetically modified to include a CBD has an increased affinity for binding cellulosic fabrics or textiles, with respect to the unmodified oxidizing enzyme. When using the modified enzyme, the conversion of indole (or an indole derivative) to indoxyl (or an indoxyl derivative) and the subsequent conversion of indoxyl (or an indoxyl derivative) to indigo (or indigo derivative) occur on the textile, whereby effectively dyeing the textile.

The use of a modified oxidizing enzyme including a CBD according to the invention allows for providing to the textile an increased amount of dye, in particular on the surface of the textile material (thus obtaining a ring-dyeing effect), with respect to the use of the unmodified oxidizing enzymes.

According to an aspect, the process of the present invention allows the production of dyed textiles. Dyed textiles obtainable through the process of the invention may have a variety of colors. In fact, advantageously, by varying the reagents (e.g., indole or a derivative thereof) in the process of the invention, different dyes, may be obtained, so that different final colors can be imparted to textiles.

Also, reagents suitable to be used in the process of the invention including waste water treatment are not expensive, so that the process of the invention is particularly cost-effective with respect to the currently available dyeing processes.

In the following description, "textile(s)" and "cellulosic textile(s)" refer to any fiber(s), yarn(s), rope(s), fabric(s) and garment(s) that include cellulosic materials and/or fibers.

As used herein, the terms "cellulose material" and "cellulosic material" refer to any cellulose-containing material. Suitable cellulose-containing materials, i.e., cellulosic materials, are e.g., in the form of filaments or fibers, such as in cotton, ramie, jute, flax (linen), viscose, rayon, modal, lyocell (Tencel™), bamboo, and mixtures thereof. Suitable cellulosic material may be also obtained from microorganisms, for example, by culturing microorganisms that produce cellulosic biopolymers. A suitable cellulosic material is microbial cellulose. According to embodiments, the textile may include one or more cellulosic material.

According to embodiments, in addition to the cellulosic material, the textile may comprise other materials (e.g., fibers) of natural origin, such as silk, wool, chitin, chitosan, and mixtures thereof.

According to embodiments, the textile may comprise materials (e.g., fibers) of synthetic origin, such as polyester, nylon, polyurethane, spandex (elastane), acrylic, modacrylic, acetate, polyolefin, vinyl and mixtures thereof.

As above mentioned, according to embodiments, the textile may be one or more textile selected from the group consisting of fiber(s), yarn(s), rope(s), fabric(s) and garment(s).

Suitable yarns may be manufactured by any known method, and suitable fabrics also may be manufactured by any known method, such as weaving, knitting, crocheting, knotting, and felting. The fabric may be a non-woven fabric. Furthermore, suitable garments may be any garment, such as jeans, shirts, casual wear garments, etc.; suitable garments may include woven denim fabrics.

According to embodiments, the textile may be a yarn or a fabric. According to embodiments, the textile is a fabric, preferably a woven fabric, more preferably a denim fabric.

As above mentioned, the process of the invention comprises a step a) of providing indole or an indole derivative to at least part of said textile.

According to the present invention, "indole derivatives", "indoxyl derivatives" and "indigo derivatives" refer to respectively indole, indoxyl and indigo substituted by one or more substituents, for example substituted by: one or more groups on one or more carbons in any position selected from positions 4, 5, 6 and 7 of indole or indoxyl, and from positions 4, 4', 5, 5', 6, 6', 7, and 7' of indigo, and/or by a group on the nitrogen atom(s) of indole, indoxyl or indigo. The one or more groups substituting one or more carbons may be groups such as, but not limited to, halogen groups, alkyl groups, alkoxy groups, aryl groups, aryloxy groups, amine groups, nitro groups and carbonyl groups. The group substituting nitrogen atom(s) may be groups such as, but not limited to, alkyl groups, aryl groups, and acyl groups. Indole derivatives may be, for example, 4-chloroindole, 5-chloroindole, 6-chloroindole, 7-chloroindole, 5-bromoindole, 6-bromoindole, 5-nitroindole, 5-hydroxyindole, 5-methylindole, 5-methoxyindole, 6-methylindole, 7-methylindole, 5-aminoindole, 1-methylindole, indole-6-carboxaldehyde; and indoxyl derivatives can be, for example, 4-chloroindoxyl, 5-chloroindoxyl, 6-chloroindoxyl, 7-chloroindoxyl, 5-bromoindoxyl, 6-bromoindoxyl, 5-nitroindoxyl, 5-hydroxyindoxyl, 5-methylindoxyl, 5-methoxyindoxyl, 6-methylindoxyl, 7-methylindoxyl, 5-aminoindoxyl, 1-methylindoxyl, indoxyl-6-carboxaldehyde. It is encompassed in the present invention also the use of any other indole and indoxyl derivatives, provided that such indole derivatives can be reacted and converted into the correspondent indoxyl derivatives by enzymatic catalysis. These indoxyl derivatives, when converted (e.g., dimerized) provide the correspondent indigo derivatives, which have each a different color. According to the present invention, the term "indigo derivatives" refers also to asymmetric indigo, i.e. indigo deriving from dimerization of two different indoxyl derivatives, or of indoxyl and an indoxyl derivative. Dyeing of the textile with asymmetric indigo can be achieved according to the process of the invention when, for example, a solution comprising two or more different indole derivatives, or indole and one or more indole derivatives, are used. As used herein, the term "indigo derivatives" refer also to asymmetric indigo, i.e. indigo deriving from dimerization of two different indoxyl derivatives, or of indoxyl and an indoxyl derivative. Dyeing of the textile with asymmetric indigo can be achieved according to the process of the invention when two or more different indole derivatives, or indole and one or more indole derivatives, are used. For example, when two different indole derivatives, or indole and an indole derivative, are used, two different indoxyl derivatives, or indoxyl and an indoxyl derivative, are obtained. Advantageously, when such two different indoxyl derivatives, or indoxyl and an indoxyl derivative, are used, three different indigo derivatives are obtained (namely, two different symmetric indigo derivatives and an asymmetric indigo derivative), so that a textile can be dyed with more than one dye, in particular, by converting such two different indoxyl derivatives, or indoxyl and an indoxyl derivative, to indigo derivatives, on the textile, whereby providing the dye onto the textile.

Indole can be provided to the textile according to methods that are known, per se, in the art, such as dipping and spraying, so that the textile is provided with indole. For example, indole can be applied to the textile according to techniques that are known in the art to be suitable to provide leuco indigo to textiles, such as, for example, rope dyeing, slasher dyeing, loop dyeing and continuous fabric dyeing techniques. In this case, at least step a) of the process of the invention may be carried out according to techniques that are well known in the art, using indole instead of leuco indigo.

Without being bound to a specific scientific explanation, when indole is provided to the textile, indole is adsorbed in the fibers of the textile. In this case, the use of an oxidizing hybrid enzyme including a cellulose-binding domain (CBD) allows to effectively obtain a ring-dyeing effect on the textile. Without being bound to a specific scientific explanation, this effect may derive from an effective conversion on indole to indigo occurring on the surface of the textile, due to the presence of the hybrid oxidizing enzyme. Also, when, in particular, dye precursors that can be negatively charged are used (e.g., tryptophan or derivative thereof) the depth of penetration of such dye precursors between the fibers of the textiles can be varied, so that different dyeing effects (e.g., ring dyeing effects) can be obtained.

According to an aspect, the process of the invention comprises a step b) of providing at least an oxidizing enzyme to at least part of the textile, whereby said at least part of textile includes said indole or indole derivative and said oxidizing enzyme, wherein the oxidizing enzyme is an oxidizing hybrid enzyme comprising a cellulose binding domain (CBD).

As used herein, the term "hybrid enzyme" refers to an enzyme which have been genetically modified to include a cellulose binding domain (CBD) or a collagen-binding domain, or a chitin-binding domain, or a chitosan-binding domain, or a domain suitable to bind synthetic polymeric materials or fibers, e.g., a polyester-binding domain. An enzyme, e.g., an oxidizing enzyme, may be modified to include a binding domain suitable for binding a material which is included into the textile to be dyed, and/or for increasing affinity for binding a material in the textile, with respect to the unmodified enzyme. For example, an enzyme that has been genetically modified to include a CBD has an increased affinity for binding cellulosic materials, with respect to the unmodified enzyme. Additionally, it is known that cellulose-binding domains (CBDs) can also bind to chitin or chitosan.

As used herein, the term "oxidizing hybrid enzyme" refers to an oxidizing enzyme which has been genetically modified to include a cellulose binding domain (CBD) or a collagen-binding domain, or a chitin-binding domain, or a chitosan-binding domain, or a domain suitable to bind synthetic polymeric materials or fibers that are present in the yarn to be dyed, e.g., a polyester-binding domain.

As used herein, "oxidizing enzyme" refers to an enzyme that is able to catalyze oxidation of its substrates, such as an oxidoreductase (EC 1). Suitable oxidoreductase is a monooxygenase (EC 1.13); it preferably is a flavin-containing monooxygenase (FMOs) (EC 1.14.13.8), and more preferably a microbial flavin-containing monooxygenase (mFMO). Alternatively, the monooxygenase can be a Baeyer-Villiger monooxygenase (BVMO). Monooxygenases, in particular FMOs and mFMOs, provide good conversion rates and binding of many dye precursors, such as indole and/or derivatives thereof, as well as a suitable specificity to convert indole derivatives, and are thus suitable to be used in the process of the invention. Baeyer-Villiger monooxygenases (BVMOs) have close homology to FMOs, and are thus suitable as well to be used in the invention. A suitable oxidizing enzyme to be used in the invention is mFMO from *Methylophaga* sp., more preferably from the strain SK1.

As used herein, the term "oxidizing enzyme" also encompasses genetically modified oxidizing enzymes that have been genetically modified to improve the enzyme's properties, such as oxidation efficiency of the substrate(s) of the oxidizing enzyme, for example, by changing one or more amino acid residues.

The oxidizing hybrid enzyme may be provided to the textile according to methods that are known, per se, in the art. According to embodiments, the oxidizing hybrid enzyme is provided to the textile by spraying or pouring, preferably by spraying.

As above mentioned, the process of the invention comprises a step c) of converting at least part of the indole or indole derivative, to indigo or indigo derivative.

Without being bound to a specific scientific explanation, it is believed that oxidizing enzymes, suitable to be used in the process of the invention, catalyze the hydroxylation of indole and/or indole derivative(s), to provide indoxyl and/or the corresponding indoxyl derivative(s), that eventually dimerize to indigo, and indigo derivatives, respectively.

According to an aspect of the invention, the oxidizing enzyme is a hybrid enzyme comprising a cellulose-binding domain (CBD).

As used herein, a typical cellulose-binding domain (CBD) may be one which occurs in a cellulase and which binds preferentially to cellulose and/or to poly- or oligosaccharide fragments thereof. Additionally, it is known that cellulose-binding domains (CBDs) can bind also to chitin and chitosan.

Cellulose binding domains and (hybrid) enzymes including such domains are known, per se in the art, for example, from document WO97/28256 and document WO97/40229. Cellulose-binding domains are polypeptide amino acid sequences which occur as integral parts of polypeptides or proteins consisting of two or more polypeptide amino acid sequence regions, for example in hydrolytic enzymes (hydrolases), which typically comprise a catalytic domain containing the active site for substrate hydrolysis and a cellulose-binding domain for binding to the cellulosic substrate in question. Such enzymes can comprise more than one catalytic domain and one, two or three cellulose-binding domains, and they may further comprise one or more polypeptide amino acid sequence regions linking the cellulose-binding domain(s) with the catalytic domain(s), a region of the latter type usually being denoted a "linker". Enzymes comprising a cellulose-binding domain are known, per se, in the art. Examples of hydrolytic enzymes comprising a cellulose-binding domain are cellulases, xylanases, mannanases, arabinofuranosidases, acetylesterases and chitinases. "Cellulose-binding domains" have also been found in algae, e.g. in the red alga *Porphyra purpurea* in the form of a nonhydrolytic polysaccharide-binding protein [see P. Tomme et al., Cellulose-Binding Domains—Classification and Properties, in: Enzymatic Degradation of Insoluble Carbohydrates, John N. Saddler and Michael H. Penner (Eds.), ACS Symposium Series, No. 618 (1996)]. However, most of the known CBDs [which are classified and referred to by P. Tomme et al. (op cit.) as "cellulose-binding domains"] derive from cellulases and xylanases. The P. Tomme et al. reference classifies more than 120 "cellulose-binding domains" into 10 families (I-X) which may have different functions or roles in connection with the mechanism of substrate binding. In proteins/polypeptides in which CBDs occur (e.g. enzymes, typically hydrolytic enzymes such as cellulases), a CBD may be located at the N or C terminus or at an internal position. That part of a polypeptide or protein (e.g. hydrolytic enzyme) which constitutes a CBD per se typically consists of more than about 30 and less than about 250 amino acid residues. For example: those CBDs listed and classified in Family I in accordance with P. Tomme et al. (op. cit.) consist of 33-37 amino acid residues, those listed and classified in Family IIa consist of 95-108 amino acid residues, those listed and classified in Family VI consist of 85-92 amino acid residues, whilst one CBD (derived from a cellulase from *Clostridium thermocellum*) listed and classified in Family VII consists of 240 amino acid residues. Accordingly, the molecular weight of an amino acid sequence constituting a CBD per se will typically be in the range of from about 4 kD to about 40 kD, and usually below about 35 kD.

In general, modified enzymes (i.e., hybrid enzymes) including a cellulose binding domain, as well as detailed descriptions of the preparation and purification thereof, are known, per se, in the art [see, e.g., WO 90/00609, WO 94/24158 and WO 95/16782, as well as Greenwood et al., Biotechnology and Bioengineering 44 (1994) pp. 1295-1305]. They may, e.g., be prepared by transforming into a host cell a DNA construct comprising at least a fragment of DNA encoding the cellulose-binding domain ligated, with or without a linker, to a DNA sequence encoding the enzyme of interest (in the present case, an oxidizing enzyme), and growing the transformed host cell to express the fused gene.

According to embodiments, type of recombinant product (i.e., enzyme hybrid) obtainable in this manner—often referred to in the art as a fusion protein—may be described by one of the following general formulae:

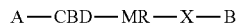

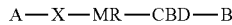

In the above formulae, CBD is an amino acid sequence comprising at least the cellulose-binding domain (CBD) per se.

MR (the middle region; a linker) may be a bond, or a linking group comprising from 1 to about 100 amino acid residues, in particular of from 2 to 40 amino acid residues, e.g. from 2 to 15 amino acid residues. MR may, in principle, alternatively be a non-amino-acid linker.

X is an amino acid sequence comprising at least the catalytically (enzymatically) active sequence of amino acid residues of an enzyme, e.g., an oxidizing enzyme, as above defined, encoded by a DNA sequence encoding the enzyme of interest.

The moieties A and B are independently optional. When present, a moiety A or B constitutes a terminal extension of a CBD or X moiety, and normally comprises one or more amino acid residues.

According to embodiments, the CBD in the genetically modified enzyme according to the present invention, may be positioned C-terminally, N-terminally or internally in the enzyme hybrid, i.e., in the genetically modified enzyme.

Hybrid enzyme of interest in the context of the invention include enzyme hybrids which comprise more than one CBD, e.g. such that two or more CBDs are linked directly to each other, or are separated from one another by means of spacer or linker sequences (consisting typically of a sequence of amino acid residues of appropriate length). Two CBDs in an enzyme hybrid of the type in question may, for example, also be separated from one another by means of an -MR—X— moiety as defined above.

According to embodiments, the hybrid enzyme may be described by the following formula:

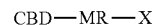

wherein:

CBD can be either the N-terminal or the C-terminal region of an amino acid sequence corresponding to at least the cellulose-binding domain; MR is the middle region (the linker), and may be a bond, or a short linking group of from about 2 to about 100 carbon atoms, in particular of from 2 to 40 carbon atoms, or typically from about 2 to about 100 amino acids, in particular of from 2 to 40 amino acids, and X can be either the N-terminal or the C-terminal region and is an enzyme, for example an oxidizing enzyme, e.g., a monooxygenase.

The above discussion made with reference to cellulose-binding domain (CBD) applies mutatis mutandis to collagen-binding domains, or chitin-binding domains, or chitosan-binding domains, or domains that bind to synthetic polymeric materials, e.g., polyester-binding domains.

Collagen-binding domains and proteins containing collagen-binding domains are known, per se, in the art. For example, a suitable collagen-binding domain may be derived from the collagenase of *Clostridium histolyticum* and it is disclosed in Nishi et al., "Collagen-binding growth factors: Production and characterization of functional fusion proteins having a collagen-binding domain", Proc. Natl. Acad. Sci. USA; Vol. 95, pp. 7018-7023, June 1998. Collagen-binding domains suitable to be used in the present invention are also disclosed in EP2940041A1 (see, e.g., par. [0024]). For example, collagen-binding domains suitable to be used in the present invention are may be derived, from fibronectin, collagenase, integrin al chain, integrin α2 chain, integrin α10 chain, integrin α11 chain, platelet glycoprotein VI, discoidin domain receptor 1, discoidin receptor 2, mannose receptor, phospholipase A2 receptor, von Willebrand factor, leukocyte-associated immunoglobulin-like receptor 1 and leukocyte-associated immunoglobulin-like receptor 2.

Chitin-binding domains and proteins containing chitin-binding domains are known, per se, in the art. For example, chitin-binding domains suitable to be used in the present invention are disclosed in EP2599790A1 (see, e.g., par. [102], Table 6 and Table 7). For example, chitin-binding domains suitable to be used in the present invention may be derived, for example, from chitinases, chitobiases and chitin-binding proteins.

Chitosan-binding domains and proteins containing chitosan-binding domains are known, per se, in the art. For example, chitosan-binding domains suitable to be used in the present invention are disclosed in EP2599790A1 (see, e.g., par. [102]) and in Chen, HP; Xu, LL, (2005) J. of Integrative Plant Biology 47(4): 452-456.

Domains that bind to synthetic polymeric materials, e.g., polyester-binding domains are known, per se, in the art. In embodiments, the domains that bind to synthetic materials may be in the form of anchor peptides. Domains that bind to synthetic polymeric materials that are suitable to be used according to the present invention are, for example, those disclosed in Islam et al., "Targeting microplastic particles in the void of diluted suspensions", Environmental International 123 (2019) 428-435. For example, domains that bind to synthetic materials suitable to be used in the present invention may be the anchor peptide LC1 and/or the anchor peptide Tachystatin A2 (TA2).

As above disclosed with reference to modified enzymes (i.e., hybrid enzymes) including a cellulose binding domain, modified enzymes (i.e., hybrid enzymes) including a collagen binding domains, chitin binding domains, chitosan binding domains and domains that bind to synthetic polymeric materials, may be produced and purified through techniques that are, per se, known in the art. For example, such hybrid enzymes may be prepared by transforming into a host cell a DNA construct comprising at least a fragment of DNA encoding the selected binding domain ligated, with or without a linker, to a DNA sequence encoding the enzyme of interest (in the present case, an oxidizing enzyme), and growing the transformed host cell to express the fused gene. Purification of the expressed hybrid enzyme may be carried out through techniques that are, per se, known in the art.

According to embodiments, the textile can include, in addition to the cellulosic material or as an alternative to the cellulosic material, collagen, chitin and/or chitosan, and synthetic materials, e.g., polyester. In this case, the oxidizing hybrid enzyme may include, in addition to the cellulose-binding domain (CBD) or in alternative to CBD, a collagen-binding domain, chitin-binding domain, a chitosan binding domain or a domain that bind to such synthetic materials, e.g., a polyester-binding domain. According to embodiments, when a tryptophanase is used, the tryptophanase may be a tryptophanase hybrid enzyme including, in addition to a CBD or in alternative to a CBD, a collagen-binding domain, chitin-binding domain, a chitosan binding domain or a domain that bind to such synthetic polymeric materials, e.g., a polyester-binding domain.

According to embodiments, in the process of the invention, the textile is provided with indole or indole derivative, i.e., an indole (derivative) is applied to the textile in an amount suitable to impart a dyeing effect. The textile treated with indole is then provided with the oxidizing hybrid enzyme. In other words, according to preferred embodiments, step a) of the process is carried out before step b). Accordingly, the textile is treated with indole and, subsequently, treated with the hybrid oxidizing enzyme. In this case, it has been observed that indole penetrates between the fibers of the textile. Once the oxidizing enzyme including a CBD is applied, it will convert indole to indigo, thereby obtaining a particularly effective dyeing of the textile, e.g., a particularly effective ring dyeing.

As above mentioned, according to embodiments, indole can be provided to the textile by conventional methods, e.g., dipping or spraying, and subsequently, the oxidizing hybrid enzyme may be provided by spraying. Subsequently, according to embodiments, the textile may be exposed to air.

According to embodiments, in the process of the invention, the textile is provided with the oxidizing hybrid enzyme and then provided with indole or indole derivative. In other words, according to embodiments, step b) of the process is carried out before step a). For example, the oxidizing hybrid enzymes may be provided to the textile by spraying and then the textile may be dipped in a bath including indole, e.g., a reaction mixture including indole. In this case, it has been observed that the oxidizing hybrid enzymes have high affinity for the cellulosic material of the textile through its cellulose-binding domain (CBD), whereby the enzymatic conversion of indole (or an indole derivative) to indoxyl (or indoxyl derivative) and the subsequent non-enzymatic conversion of indoxyl (or indoxyl derivative) to indigo (or indigo derivative) occurs on the textile, so that substantially all the indigo obtained is provided to the textile.

According to embodiments, the process of the invention may include a step of opening the fibers of the textile during step a) of providing indole and/or during step b) of providing the enzyme. Fibers of a textile can be opened, e.g., by increasing the space between a fiber and another, according to techniques that are known, per se, in the art. In this case, penetration of indole and/or of the enzymes is particularly effective.

According to embodiments, at least part of said indole or indole derivative and/or at least part of said indigo and/or indigo derivative is located between the fibers of said textile.

Oxidizing enzymes require $O_2$, i.e. oxygen, in order to catalyze the hydroxylation of indole or its derivative to indoxyl or indoxyl derivatives. The $O_2$ required, can be the oxygen normally dissolved within, for example, in the aqueous indole solution, and/or in the aqueous mixture including the oxidizing enzyme.

Conversion of indoxyl to indigo can occur spontaneously, when, for example, $O_2$ concentration is in an adequate amount to oxidize indoxyl or its derivatives. The $O_2$ required, can be the atmosphere oxygen and/or the oxygen normally dissolved within, for example, the indole solution, and/or in the aqueous mixture including the oxidizing enzyme.

According to embodiments, step c) of converting at least part of the indole to indigo is carried out in presence of oxygen ($O_2$), for example, exposing the textile to oxygen, e.g., to air.

According to embodiments, at least step b) of providing the enzyme and/or step c) of converting indole to indigo may be carried out in inert or substantially inert atmosphere, e.g., in an atmosphere with reduced amount of oxygen to delay the conversion of indoxyl to indigo.

After the textile is provided with indigo or a derivative thereof, it may be washed and/or rinsed, e.g., to remove the oxidizing hybrid enzyme from the cellulosic material, e.g., from cotton fibers, and dried.

Removal of the enzyme from the textile may be carried out by changing pH and/or temperature. Indeed, an enzyme that is immobilized to, for example, a cellulosic material (e.g., cotton) through a CBD, can remain on the cellulosic material for several days (e.g., 7-10 days), when the pH is in the range between about 3 and about 8, and/or the temperature is between about 4° C. to about 50° C.

Thus, a change of pH and/or temperature can be applied to remove the hybrid enzyme from the cellulosic material, e.g., raising the pH (for example, on the surface of the fabric) above 8, and or raising the temperature above 50° C.

According to embodiments, the process further comprises a step d) of removing at least the oxidizing hybrid enzyme from the textile, preferably by washing and/or rinsing the textile at a pH lower than about 3 or higher than about 8 and/or to a temperature lower than about 4° C. or higher than about 50° C.

Suitable oxidizing enzymes are oxygenases that are capable to hydroxylate indole or indole derivatives to obtain indoxyl or indoxyl derivatives. According to embodiments, the oxidizing enzyme is an oxygenase, preferably a monooxygenase, more preferably is a flavin-containing monooxygenases (FMO).

According to embodiments, the oxidizing hybrid enzyme is CBD-FMO, preferably CBD-mFMO.

According to embodiments, a textile including a cellulosic material is provided with indole or an indole derivative, at least an oxidizing hybrid enzyme, suitable cofactors, and optionally one or more cofactor regenerating enzymes.

According to embodiments, the aqueous mixture including the enzyme(s) may comprise functional solutes, such as salts, buffering agents and oxygen and/or peroxide scavengers (e.g. catalases). Catalase may be provided to convert possibly formed $H_2O_2$ into $O_2$ and $H_2O$.

According to embodiments, indole is applied to the textile as an indole precursor. Namely, according to embodiments, step a) of the process of the invention comprises a step of providing tryptophan or a tryptophan derivative, and at least a tryptophanase, to the textile, and converting said tryptophan or tryptophan derivative to obtain the indole or indole derivative. When tryptophan is used, a better ring-dyeing effect can be obtained, in particular when the textile includes cellulosic materials. Without being bound to a specific scientific explanation, this effect may derive from the fact that, in view of their properties, tryptophan and tryptophan derivatives, when provided to the textile, will be predominantly localized on the surface of the textile (in particular when the textile includes at least a cellulosic material), thus providing an improved ring effect.

In other words, tryptophan and/or a tryptophan derivative can be provided to the textile instead of, or in addition to, indole or indole derivatives. In this case, at least a tryptophanase may be provided to the textile, in addition to the oxidizing hybrid enzyme, to convert at least part of the tryptophan to indole. According to embodiments, tryptophan and/or a tryptophan derivative can be used as starting material (i.e., starting substrate) in the process of the invention, to enzymatically produce indole or indole derivatives. Accordingly, tryptophan and/or a tryptophan derivative can be used as starting materials (i.e., starting substrates) to obtain indigo and/or indigo derivatives, through enzymatic reactions.

Tryptophanases (systematic name: L-tryptophan indole-lyase (deaminating; pyruvate-forming)) are enzymes, per se known, that cleave a carbon-carbon bond of tryptophan, releasing indole. They may use pyridoxal phosphate (PLP) as cofactor. According to embodiments of the invention, PLP can be optionally used to improve the yield of the enzymatic conversion of tryptophan or of its derivatives catalyzed by tryptophanase. Tryptophanases suitable to be used in the process of the invention are known in the art. For example, a tryptophanase suitable to be used in the method of the invention is the tryptophanase of *Escherichia coli* NEB® 10β.

As used herein, the term "tryptophan derivative" refers to tryptophan substituted with one or more substituents, as above disclosed, mutatis mutandis, with reference to indole, indoxyl and indigo derivatives. For example, a tryptophan derivative may be a halogenated derivative of tryptophan, i.e., halogenated tryptophan (e.g., 6-bromotryptophan).

According to embodiments, the tryptophan derivative is a 6-bromotryptophan (i.e., a halogenated tryptophan) and the indigo derivative is Tyrian purple.

As used herein, the term "halogenated derivative" refers to any tryptophan, indole, indoxyl and indigo substituted with a halogen atom, in particular fluorine, chlorine, bromine or iodine atom, on one or more carbons in position 5, 6, 7 and 8 (and also 5', 6', 7' and 8' for indigo).

According to embodiments, the textile may be provided with tryptophan or a tryptophan derivative, a tryptophanase, an oxidizing hybrid enzyme, suitable cofactors, and optionally one or more cofactor regenerating enzymes. Tryptophan is enzymatically converted to indole by the tryptophanase. Indole is converted to indoxyl by the oxidizing hybrid enzyme. Indoxyl is (non-enzymatically) converted (e.g., dimerized) to indigo, to dye the textile.

As above discussed with reference to indole, tryptophan can be provided to the textile according to methods that are known, per se, in the art, such as dipping and spraying. Suitable techniques for providing tryptophan to the textile are techniques that are known in the art to be suitable to provide leuco indigo to textiles, such as, for example, rope dyeing, slasher dyeing, loop dyeing and continuous fabric dyeing techniques. In this case, at least the step of providing tryptophan to the textile of the process of the invention, may be carried out according to techniques that are well known in the art for impregnating textiles with leuco indigo, but using tryptophan instead of leuco indigo.

According to embodiments, the textile (e.g., a yarn or a fabric) may be treated, e.g., impregnated, with tryptophan and subsequently provided with at least a tryptophanase (e.g., by spraying), to convert tryptophan to indole. Subsequently, the textile may be provided with the oxidizing hybrid enzyme (e.g., by spraying) to convert indole to indoxyl to obtain indigo.

In other words, according to embodiments, tryptophanase may be provided to the textile before the oxidizing hybrid enzyme. In this case, according to embodiments, tryptophanase is preferably not removed from the textile before providing the oxidizing enzyme.

According to embodiments, at least part of the oxidizing hybrid enzyme is provided to the textile together with said tryptophanase.

In other words, according to embodiments, the textile may be treated, e.g., impregnated, with tryptophan and subsequently provided (e.g., by spraying) with a mixture of at least a tryptophanase and at least an oxidizing hybrid enzyme, thereby converting tryptophan to indigo.

According to embodiments, the tryptophanase is a tryptophanase hybrid enzyme comprising a cellulose-binding domain (CBD).

According to embodiments, enzymes may be removed from the textile by washing and/or rinsing, preferably at a pH lower than about 3 or higher than about 8 and/or to a temperature lower than about 4° C. or higher than about 50° C.

One or more of the enzymes used in the process of the invention may require one or more cofactors.

As used herein, the term "cofactor" refers to a non-protein chemical compound that is required for an enzyme's activity as a catalyst. Cofactors can be divided into two types, either inorganic ions, or complex organic molecules called coenzymes. For sake of clarity, in the present description, the term "cofactor" is used to indicate any non-protein chemical compound that is required for an enzyme's activity, according to the protein of the invention, without restriction to a specific chemical class of molecules, i.e., including both organic and inorganic molecules.

According to embodiments, cofactor regenerating enzymes may be used to regenerate the cofactor(s) which may be needed by the enzymes used in the process of the invention.

In this case, advantageously, expensive cofactors (e.g., NADPH) are regenerated by consuming inexpensive cofactors (such as glucose, phosphite or formate).

For example, oxidizing enzymes such as FMOs may use NADPH as cofactor which may be produced by the NADPH regenerating enzyme that uses cheap cofactors such as glucose, phosphite and formate.

According to embodiments, the step of hydroxylating indole (or an indole derivative) in the presence of at least an oxidizing hybrid enzyme, to obtain indoxyl or an indoxyl derivative, may be carried out in the presence of at least an enzyme suitable for regenerating the cofactor, required by the oxidizing enzyme. For example, when the oxidizing enzyme is a monooxygenase, NADPH may be used as cofactor.

According to embodiments, the oxidizing enzyme may be coupled to a cofactor-regenerating enzyme, preferably fused to a cofactor-regenerating enzyme.

In other words, according to embodiments, the oxidizing enzyme may be a fusion enzyme wherein the oxidizing enzyme is fused to a cofactor-regenerating enzyme. In this case, the oxidizing hybrid enzyme comprising a cellulose-binding domain is fused to a cofactor-regenerating enzyme, i.e., further comprises a cofactor-regenerating enzyme. For example, if the oxidizing enzyme is a microbial flavin-containing monooxygenase (mFMO), and the cofactor-regenerating enzyme is phosphite dehydrogenase (PTDH), the oxidizing hybrid enzyme may be described by the following formula:

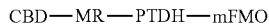

wherein
CBD can be either the N-terminal or the C-terminal region of an amino acid sequence corresponding to at least the cellulose-binding domain; MR is the middle region (the linker), and may be a bond, or a short linking group of from about 2 to about 100 carbon atoms, in particular of from 2 to 40 carbon atoms, or typically from about 2 to about 100 amino acids, in particular of from 2 to 40 amino acids, PTDH is the cofactor-regenerating enzyme, and mFMO is the monooxygenase, and can be either the N-terminal or the C-terminal region.

According to embodiments, the cofactor-regenerating enzyme is selected from the group consisting of glucose dehydrogenase (GDH), phosphite dehydrogenase (PTDH), and formate dehydrogenase (FDH), and preferably is PTDH. In embodiments, the cofactor-regenerating enzyme is suitable to regenerate NADPH and/or NADH cofactor.

According to embodiments, the cofactor regenerating enzyme can be a mutant that has improved activity. For example, the NADPH regenerating enzyme can be a mutant that has improved NADPH production, e.g. PTDH disclosed in WO 2004/108912 A2.

According to embodiments, when, for example, the oxidizing enzyme is mFMO and the cofactor-regenerating enzyme is PTDH, the hybrid oxidizing enzyme may include the fusion enzyme PTDH-mFMO, wherein mFMO and/or PTDH have been genetically modified to include a cellulose binding domain (CBD).

According to embodiments, the oxidizing hybrid enzyme comprises an oxidase, a cellulose binding domain, and further comprises a cofactor regenerating enzyme, preferably PTDH.

According to embodiments of the process of the invention, indole or indole derivatives may be obtained by converting tryptophan, or a tryptophan derivative, in the presence of a tryptophanase, and PLP may be used as cofactor in the reaction catalyzed by the tryptophanase.

As above discussed, an enzyme, e.g., an oxidizing enzyme, may be modified to include a binding domain suitable for binding a material which is included into the textile to be dyed, and/or for increasing affinity for binding a material in the textile, with respect to the unmodified enzyme. For example, it has been observed that an enzyme that has been genetically modified to include a CBD has an increased affinity for binding cellulosic materials, with respect to the unmodified enzyme. Additionally, it has also be observed that cellulose-binding domains (CBDs) can also bind to chitin or chitosan. According to embodiments, a hybrid enzyme, e.g., an oxydizing hybrid enzyme and/or a tryptophanase hybrid enzyme may include a cellulose binding domain (CBD) or a collagen-binding domain, or a chitin-binding domain, or a chitosan-binding domain, or a domain suitable to bind synthetic polymeric materials or fibers, e.g., a polyester-binding domain.

An object of the present is therefore a process for dyeing a textile including collagen, comprising the following steps:
 a) providing indole or an indole derivative to at least part of the textile;
 b) providing at least an oxidizing enzyme to at least part of the textile, whereby said at least part of textile includes said indole or indole derivative and said oxidizing enzyme;
 c) converting at least part of the indole or indole derivative to indigo or indigo derivative, thereby dyeing at least part of the textile;
wherein said oxidizing enzyme is an oxidizing hybrid enzyme comprising a collagen-binding domain.

Also, an object of the present invention is a process for dyeing a textile including chitin and/or chitosan, comprising the following steps:
 a) providing indole or an indole derivative to at least part of the textile;
 b) providing at least an oxidizing enzyme to at least part of said textile, whereby said at least part of textile includes said indole or indole derivative and said oxidizing enzyme;
 c) converting at least part of the indole or indole derivative to indigo or indigo derivative, thereby dyeing at least part of the textile;
wherein said oxidizing enzyme is an oxidizing hybrid enzyme comprising a chitin-binding domain or a chitosan binding domain or a cellulose binding domain (CBD).

A further object of the present invention is a process for dyeing a textile including a synthetic polymeric material, preferably polyester, comprising the following steps:
 a) providing indole or an indole derivative to at least part of the textile;
 b) providing at least an oxidizing enzyme to at least part of said textile, whereby said at least part of textile includes said indole or indole derivative and said oxidizing enzyme;
 c) converting at least part of the indole or indole derivative to indigo or indigo derivative, thereby dyeing at least part of said textile;
wherein said oxidizing enzyme is an oxidizing hybrid enzyme comprising a synthetic polymeric material-binding domain, preferably a polyester-binding domain.

The above discussion made with reference to the process for dyeing textiles including a cellulosic material, also applies to the above-mentioned processes for dyeing textiles including collagen, chitin and/or chitosan, and a synthetic polymeric material, preferably polyester.

Another object of the present invention is a dyed textile as obtainable according to the process of the invention.

According to embodiments, the textile is a yarn or a plurality of yarns, such as, for example, a rope.

According to embodiments, the textile is a fabric, preferably a woven fabric, more preferably a twill fabric.

According to embodiments, the textile obtained through the process of the invention is indigo dyed.

A further object of the present invention is an oxidizing hybrid enzyme, namely a modified enzyme comprising at least an oxidizing enzyme, preferably an oxygenase, a cellulose binding domain or a collagen-binding domain, or a chitin-binding domain, or a chitosan binding domain, or a synthetic polymeric material-binding domain.

An exemplary synthetic material binding domain is polyester binding domain.

According to embodiments, the hybrid enzyme further comprises a cofactor-regenerating enzyme.

According to embodiments, the oxygenase is a monooxygenase, preferably mFMO, and the cofactor regenerating enzyme is PTDH.

As above mentioned, it has been observed that the use of a modified oxidizing enzyme including a CBD according to the invention allows for providing to the textile an increased amount of dye with respect to the use of the unmodified oxidizing enzymes.

A further object of the invention is a tryptophanase hybrid enzyme comprising a tryptophanase, and a cellulose-binding domain (CBD) or a collagen-binding domain, or a chitin-binding domain, or a chitosan binding domain, or a synthetic polymeric material-binding domain. An exemplary synthetic material binding domain is polyester binding domain.

Binding domains suitable to bind to synthetic materials, e.g., synthetic materials different from polyester, may be designed and produced according to techniques that are known, per se, in the art.

The process of the invention provides the synthesis of indigo or an indigo derivative, optionally starting from tryptophan or a tryptophan derivative, by means of the combination of at least an enzymatic reaction step carried out by the oxidizing hybrid enzyme, and a non-enzymatic step. The process of the invention is particularly advantageous to provide indigo and/or indigo derivatives, such as Tyrian purple, to textiles, whereby dyeing at least part of such textiles, in a cost-effective way.

Methods for the preparation and the purification of hybrid enzymes according to the present invention, are known, per se, in the art. According to embodiments, the oxidizing hybrid enzyme and/or the tryptophanase and/or the tryptophan halogenase are isolated enzymes, preferably purified enzymes.

As used herein, the term "purified" refers to enzymes free from other components from the organism from which the enzymes are derived.

According to embodiments, a textile including a cellulosic material is provided with indole or an indole derivative and with a reaction mixture, comprising, in a suitable buffer, an oxidizing hybrid enzyme and suitable cofactors. Preferably, the textile is provided with indole or indole derivatives and, subsequently, with an aqueous mixture including the oxidizing hybrid enzyme. Preferably, the oxidizing hybrid enzyme (e.g., an aqueous mixture including the oxidizing hybrid enzyme) is provided to the fabric by spraying or pouring.

According to preferred embodiments, the indole may be provided to the by spraying or pouring, or textile may be immersed in a mixture comprising indole or an indole derivative. Subsequently the oxidizing hybrid enzyme may be sprayed or poured onto the textile.

According to other embodiments, the textile may be provided with a mixture comprising the oxidizing hybrid enzyme (e.g., by spraying or pouring), and subsequently the textile may be provided with indole or an indole derivative.

According to embodiments, aqueous mixtures comprising indole and/or enzymes may include suitable buffers, suitable cofactors, functional solutes, such as salts, and oxygen and/or peroxide scavengers (e.g. catalases).

For example, the textile may be provided with indole and, subsequently, provided with a mixture including, in a suitable buffer, a monooxygenase hybrid enzyme, one or more cofactors, one or more cofactor regenerating enzymes and optionally a catalase. In embodiments, the monooxygenase hybrid enzyme is fused with a cofactor regenerating enzyme, such as, for example, CBD-linker-PTDH-mFMO.

According to the present invention, all the enzymes used in the process in the process of the invention may be genetically engineered.

Methods and processes for the production of genetically engineered enzymes, as well as for the production of hybrid or fusion enzymes are known, per se, in the art.

According to embodiments, indole and enzymes may be separately provided to the textile as aqueous mixtures. Such aqueous mixtures may have pH from about 5 to about 8, preferably from 5.5 to 8, more preferably between 6 and 7.5. Such aqueous medium may comprise a buffering agent, for example a potassium phosphate buffer.

According to embodiments, the process may be carried out at temperature comprised in the range from 20° C. to 50° C., preferably from 25° C. to 40° C.

According to embodiments, the process may be carried out, for example, for a time that is sufficient to obtain a suitable amount of dye. For example, the process may per carried out for a time comprised between a few hours to several days, for example, 3-5 days.

In embodiments, temperature, pH values and duration of the process can vary and can be those conventionally used in enzymatic synthesis of insoluble dyes.

In embodiments, temperature, pH values and duration of the process, as well as other parameters can be adjusted according to, for example, which type of textile has to be dyed and which dye is chosen as a final dye.

A further object of the invention is a textile comprising an oxidizing hybrid enzyme and/or a tryptophanase hybrid enzyme.

According to embodiments, a textile comprising an oxidizing enzyme according to the invention may be undyed or at least in part dyed.

According to embodiments, a textile comprising a tryptophanase hybrid enzyme may be undyed, in particular when the textile is not provided with an oxidizing hybrid enzyme.

The present invention relates to a process wherein one or more dye precursors (e.g., tryptophan, indole or derivatives thereof) are provided to a textile and converted by one or more enzymes (e.g., a tryptophanase and an oxidizing enzyme) to provide the textile with a dye, preferably indigo and/or one or more indigo derivatives, e.g., one or more indigoid dyes.

In particular, the present invention relates to a process for dyeing a textile, comprising the following steps:

a) providing at least one dye precursor to at least part of said textile;

b) providing one or more enzymes to at least part of said textile, whereby said at least part of textile includes said dye precursor and said enzyme;

c) converting at least part of said dye precursor to a dye, thereby dyeing at least part of said textile;

wherein said one or more enzymes include an oxidizing hybrid enzyme comprising a cellulose-binding domain (CBD).

According to an aspect, the textile includes a cellulosic material. According to embodiments, in addition to the cellulosic material or as an alternative to the cellulosic material, the textile may comprise one or more of collagen, chitin, chitosan, and synthetic polymeric materials, e.g., polyester. In this case, the oxidizing hybrid enzyme may include, a cellulose-binding domain (CBD) or a collagen-binding domain, or a chitin-binding domain, or a chitosan binding domain or a domain that bind to such synthetic polymeric materials, e.g., a polyester-binding domain.

According to embodiments, the dye precursor may be selected from tryptophan, a tryptophan derivative, indole, an indole derivative, and mixtures thereof.

When the dye precursor includes tryptophan or a tryptophan derivative, said one or more enzymes include a tryptophanase.

In embodiments, the dye precursor may be provided to the textile according to methods that are known, per se, in the art, such as dipping and spraying, so that the textile is impregnated with the dye precursor. For example, the dye precursors can be provided according to techniques that are known in the art to be suitable to provide leuco indigo to textiles, such as, for example, rope dyeing, slasher dyeing, loop dyeing and continuous fabric dyeing techniques.

In embodiments, the enzymes may be provided to the textile according to methods that are known, per se, in the art, e.g., dipping and spraying. According to embodiments, one or more enzymes may be provided to the textile by spraying or pouring. Preferably, the oxidizing enzyme is provided to the textile by spraying.

According to embodiments, the enzymes (e.g., aqueous mixtures comprising enzymes), may be provided to a yarn or elongated element through the process discloses in the European patent application number EP3581705A1, in the name of the present applicant. Although EP3581705A1 relates to a process for providing a culture of microorganisms the process disclosed therein may be applied, mutatis mutandis, to provide enzymes to yarns or elongated elements.

For example, an aqueous mixtures comprising enzymes suitable to be used in the present invention, may be provided to a yarn, which has been previously provided with a dye precursor, by means of an apparatus comprising a feeding device having an outlet for dispensing such aqueous mixture from the outlet, and a yarn source to supply a yarn, that is treated with at least a dye precursor, to the feeding device, wherein the apparatus is configured so that the aqueous mixture contacts at least part of the yarn when the mixture is dispensed from the outlet. The dispensing of the mixture may be adjusted so that the mixture is dispensed from the outlet of the feeding device at a flow rate selected so that the mixture envelops the yarn but is prevented from falling from the yarn, and from drying out at the outlet.

According to embodiments, the dye precursor is preferably provided to the textile before the one or more enzymes.

According to embodiments, the process of the invention may include the following steps:

a) providing tryptophan or a tryptophan derivative to at least part of a textile;

b) providing at least a tryptophanase and at least an oxidizing enzyme to at least part of said textile, whereby said at least part of textile includes said tryptophan, said tryptophanase and said oxidizing enzyme;

c) converting at least part of said tryptophan or tryptophan derivative to indigo or indigo derivative, thereby dyeing at least part of said textile;

wherein at least said oxidizing enzyme is a hybrid enzyme comprising a cellulose-binding domain (CBD).

According to embodiments, when the dye precursor is tryptophan or a tryptophan derivative, the tryptophanase is provided to the textile before the oxidizing hybrid enzyme. In this case, tryptophanase is preferably not removed from the textile before providing the oxidizing enzyme.

According to embodiments, when the dye precursor is tryptophan or a tryptophan derivative the tryptophanase and the oxidizing hybrid enzymes are provided together to the textile.

According to an aspect of the present invention, at least the oxidizing enzyme is a hybrid enzyme including a binding domain that is suitable to bind the enzyme to the textile and/or increase the affinity of the enzyme for the textile, namely to a material that is included into the textile to be dyed, with respect to the unmodified enzyme. For example, an enzyme may be genetically modified to include a cellulose binding domain (CBD) or a collagen-binding domain, or a chitin-binding domain, or a chitosan-binding domain or a domain suitable to bind synthetic polymeric materials or fibers, e.g., a polyester-binding domain. For example, when the textile to be dyed includes a cellulosic material, at least the oxidizing enzyme is an oxidizing enzyme that has been genetically modified to include a cellulose binding domain (CBD). In embodiments, the tryptophanase may be a tryptophanase hybrid enzyme.

When the dye precursor is tryptophan or a tryptophan derivative, at least part of a textile may be provided with said dye precursor and subsequently provided with at least a tryptophanase and at least an oxidizing hybrid enzyme. Tryptophan is enzymatically converted to indole by the tryptophanase, and indole is enzymatically converted to indoxyl by the oxidizing enzyme. Indoxyl in non-enzymatically converted to indigo, thereby dyeing the textile.

When the dye precursor is indole or an indole derivative, at least part of a textile may be provided with said dye precursor and subsequently provided with at least an oxidizing hybrid enzyme. Indole is enzymatically converted to indoxyl by the oxidizing enzyme, and indoxyl in non-enzymatically converted to indigo, thereby dyeing the textile.

The invention claimed is:

1. A hybrid enzyme comprising an oxidizing enzyme and a cellulose-binding domain (CBD), said hybrid enzyme being cellulose-binding domain-flavin-containing monooxygenase (CBD-FMO).

2. The oxidizing hybrid enzyme according to claim 1, further comprising a cofactor regenerating enzyme.

3. A textile comprising a hybrid enzyme according to claim 1.

4. The oxidizing hybrid enzyme according to claim 2, wherein said cofactor regenerating enzyme is PTDH.

5. A hybrid enzyme comprising an oxidizing enzyme and at least one binding domain, wherein said oxidizing enzyme is a flavin-containing monooxygenase (FMO), and wherein said oxidizing hybrid enzyme is selected from collagen-binding domain-flavin-containing monooxygenase, chitin-binding domain-flavin-containing monooxygenase, chitosan-binding domain-flavin-containing monooxygenase, polyester-binding domain-flavin-containing monooxygenase and binding domain for a synthetic polymeric material-flavin-containing monooxygenase.

* * * * *